United States Patent [19]
Tsuruta

[11] Patent Number: 4,715,726
[45] Date of Patent: Dec. 29, 1987

[54] METHOD OF MEASURING THE STRENGTH OF CONCRETE FOR SLIP FORM PROCESS

[75] Inventor: Kenji Tsuruta, Nagareyama, Japan

[73] Assignee: Ohbayashi-Gumi, Ltd., Osaka, Japan

[21] Appl. No.: 877,972

[22] Filed: Jun. 23, 1986

[30] Foreign Application Priority Data

Nov. 1, 1985 [JP] Japan .............................. 60-244086
May 19, 1986 [JP] Japan .............................. 61-112734

[51] Int. Cl.$^4$ .............................................. G01N 3/00
[52] U.S. Cl. ...................................... 374/102; 374/53; 364/506
[58] Field of Search ...................... 73/786, 78; 374/53, 374/45, 54, 102, 103, 141; 364/506, 550

[56] References Cited

U.S. PATENT DOCUMENTS

| | | | |
|---|---|---|---|
| 4,076,778 | 2/1978 | Whitting | 264/33 |
| 4,108,583 | 8/1978 | Ellen | 249/22 |
| 4,480,929 | 11/1984 | Hansen | 374/54 |
| 4,566,806 | 1/1986 | De Bondt | 374/53 |

FOREIGN PATENT DOCUMENTS

1286262 8/1972 United Kingdom ................ 374/102

*Primary Examiner*—Stewart J. Levy
*Assistant Examiner*—Robert R. Raevis
*Attorney, Agent, or Firm*—Wenderoth, Lind & Ponack

[57] ABSTRACT

A method of measuring the strength of concrete for the slip form process, to determine upward movement of a slide form so that the concrete poured in the slide form will be released therefrom after setting to a degree of strength capable of maintaining the shape of a structure to be constructed. According to the method, an arithmetic unit calculates the temperature integral of the concrete poured in the slide form on the basis of measured data given thereto by a temperature sensor having a plurality of measuring elements and inserted into the concrete and by an altimeter that measures the position of the slide form. The strength of the concrete is determined from the known relation between the temperature integral and the strength of the concrete.

11 Claims, 16 Drawing Figures

| time | $t_{(i)}$ | $t_{(i+1)}$ | $t_{(i+2)}$ | $t_{(i+3)}$ | $t_{(i+4)}$ | $t_{(i+5)}$ | $t_{(i+6)}$ | $t_{(i+7)}$ | $t_{(i+8)}$ |
|---|---|---|---|---|---|---|---|---|---|
| A |  |  |  |  | $T_{A(i+4)}$ | $T_{A(i+5)}$ | $T_{A(i+6)}$ | $T_{A(i+7)}$ | $T_{A(i+8)}$ |
| B |  |  |  | $T_{B(i+3)}$ | $T_{B(i+4)}$ | $T_{B(i+5)}$ | $T_{B(i+6)}$ | $T_{B(i+7)}$ | $T_{B(i+8)}$ |
| C |  |  | $T_{C(i+2)}$ | $T_{C(i+3)}$ | $T_{C(i+4)}$ | $T_{C(i+5)}$ | $T_{C(i+6)}$ | $T_{C(i+7)}$ | $T_{C(i+8)}$ |
| D |  | $T_{D(i+1)}$ | $T_{D(i+2)}$ | $T_{D(i+3)}$ | $T_{D(i+4)}$ | $T_{D(i+5)}$ | $T_{D(i+6)}$ | $T_{D(i+7)}$ | $T_{D(i+8)}$ |
| E | $T_{E(i)}$ | $T_{E(i+1)}$ | $T_{E(i+2)}$ | $T_{E(i+3)}$ | $T_{E(i+4)}$ | $T_{E(i+5)}$ | $T_{E(i+6)}$ | $T_{E(i+7)}$ | $T_{E(i+8)}$ |

| time | $T_{A(i)}$ | $T_{A(i+1)}$ $T_{B(i+1)}$ | $T_{A(i+2)}$ $T_{B(i+2)}$ $T_{C(i+2)}$ | $T_{A(i+3)}$ $T_{B(i+3)}$ $T_{C(i+3)}$ $T_{D(i+3)}$ | $T_{A(i+4)}$ $T_{B(i+4)}$ $T_{C(i+4)}$ $T_{D(i+4)}$ $T_{E(i+4)}$ |
|---|---|---|---|---|---|
| | $t_{(i)}$ | $t_{(i+1)}$ | $t_{(i+2)}$ | $t_{(i+3)}$ | $t_{(i+4)}$ |

FIG. 8
(B)

| | | | | | $T_{A(i+4)}$ |
|---|---|---|---|---|---|
| | | | | $T_{A(i+3)}$ | $T_{B(i+4)}$ |
| | | | $T_{A(i+2)}$ | $T_{B(i+3)}$ | $T_{C(i+4)}$ |
| | | $T_{A(i+1)}$ | $T_{B(i+2)}$ | $T_{C(i+3)}$ | $T_{D(i+4)}$ |
| | $T_{B(i)}$ | $T_{B(i+1)}$ | $T_{C(i+3)}$ | $T_{D(i+3)}$ | $T_{E(i+4)}$ |
| time | $t_{(i)}$ | $t_{(i+1)}$ | $t_{(i+2)}$ | $t_{(i+3)}$ | $t_{(i+4)}$ |

FIG. 8
(C)

| | | | | | $T_{A(i+4)}$ |
|---|---|---|---|---|---|
| | | | | $T_{A(i+3)}$ | $T_{B(i+4)}$ |
| | | | $T_{A(i+2)}$ | $T_{B(i+3)}$ | $T_{C(i+4)}$ |
| | | $T_{B(i+1)}$ | $T_{B(i+2)}$ | $T_{C(i+3)}$ | $T_{D(i+4)}$ |
| | $T_{C(i)}$ | $T_{C(i+1)}$ | $T_{C(i+2)}$ | $T_{D(i+3)}$ | $T_{E(i+4)}$ |
| time | $t_{(i)}$ | $t_{(i+1)}$ | $t_{(i+2)}$ | $t_{(i+3)}$ | $t_{(i+4)}$ |

METHOD OF MEASURING THE STRENGTH OF CONCRETE FOR SLIP FORM PROCESS

BACKGROUND OF THE INVENTION

1. Field of the Invention

The present invention relates to a method of measuring the strength of concrete for the slip form process and, more specifically, to a method of measuring the strength of concrete on the basis of an integral of concrete temperature as a function of time, as concrete pouring progresses.

2. Description of the Prior Art

As is generally known, the slip form process is applied extensively to building tower concrete structures such as elevated tanks, tall storage bins and silos.

In the slip form process, relatively short form panels are assembled side by side to construct a slide form. Concrete is progressively poured in the slide form while the slide form is moved upward slowly by means of rods buried in the poured concrete which, when hardened, consititues the wall of the stucture. Naturally, the concrete already poured must have a sufficient strength to support itself and the slide form to allow the slide form to be moved upward. The strength of concrete increases gradually with the lapse of time after pouring. The rate of increase is dependent on the ambient conditions, such as the atmospheric temperature, himidity and weather conditions. Accordingly, in the slip form process, it is necessary to measure the strength of the concrete poured in the slide form as concrete pouring progresses in a manner, for example, as disclosed in Japanese Patent Publication No. 52-16336.

According to a measuring method disclosed in the above-mentioned Japanese patent publication, a pressing member is pressed against the concrete poured in the slide form to determine the strength of concrete on the basis of the relation between the stress that acts on the pressing member and the amount of displacement of the pressing member under the pressure applied thereto. However, this method involves disadvantages in that depressions tend to be formed and remain in the surface of the concrete structure by the pressing member, and that it is impossible to measure the strength during elevational movement of the slide form.

Japanese Patent Laid-Open No. 59-118961 discloses an automatic control of elevational movement of the slide form on the basis of measured strength of concrete poured in the slide form. The strength is measured by inserting a sensor into the concrete, and a signal from the sensor is forwarded to a comparator to determine whether the strength is sufficient in view of a predetermined value. This prior art, however, does not suggest how the sensor can measure the strength.

Further, Japanese Patent Laid-Open No. 60-199164 shows a method of measuring strength by inserting a rod into the poured concrete. The rod is inserted under a predetermined stress, and an amount of displacement of the rod indicates a level below which the concrete is considered to have a sufficient strength. This method requires that the stress applied to the rod must exactly be set to a predetermined value so as to avoid destruction of the hardened concrete, however, this is practically difficult.

SUMMARY OF THE INVENTION

The present invention has been made in view of the above problems of the prior art. Accordingly, it is an object of the present invention to provide a method of measuring the strength of concrete for the slip form process, capable of measuring the strength of the concrete poured in a slide form without producing any flaw in the concrete structure even while the slide form is being moved upward.

According to the present invention, in a slip form process in which a slide form is moved upward after concrete poured therein has set to a degree to provide sufficient strength, a method of measuring the strength of concrete comprises the steps of: measuring a temperature of the concrete by a temperature sensor movable with the slide form and inserted into the concrete, the sensor having arranged in an axial direction thereof a plurality of measuring elements; measuring a position of the slide form by an altimeter; calculating an integral of the temperature and a time during which the temperature has been measured, by an arithmetic unit on the basis of data given by the temperature sensor and the altimeter; and determining the strength of the concrete based on the integral.

The relation between the integral of temperature and time and the strength of concrete is known accurately. Therefore, the strength of concrete can be accurately determined on the basis of the temperature integral. Furthermore, since the temperature sensor moves upward with the slide form, the strength can be continuously measured without interruption.

BRIEF DESCRIPTION OF THE DRAWINGS

The above and other objects, features and advantages of the present invention will become more apparent from the following description when taken in conjunction with the accompanying drawings, in which.

DETAILED DESCRIPTION OF THE INVENTION

Preferred embodiments of the present invention will be described hereinafter with reference to the accompanying drawings.

FIGS. 1 to 4 are illustrations of assistance in explaining a method of measuring the strength of concrete for the slip form process, in a first embodiment, according to the present invention.

Figure 1:
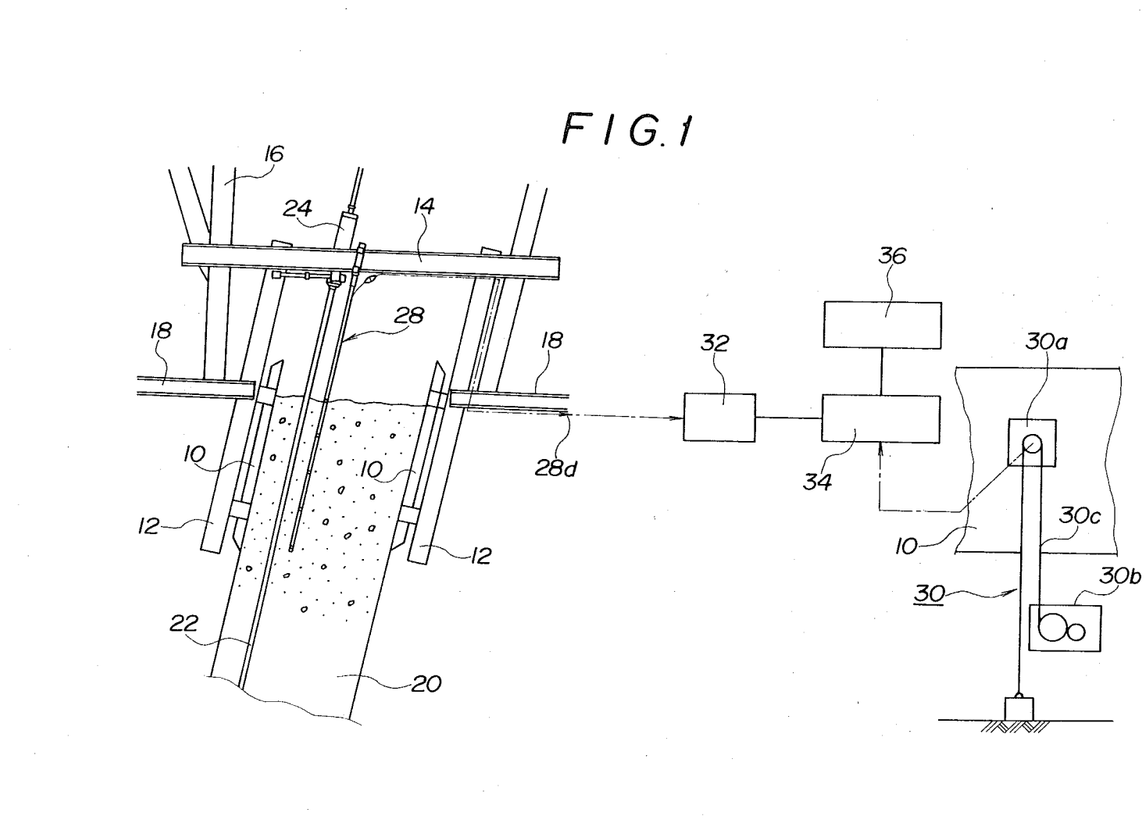
FIG. 1 is a schematic illustration for explanation of a slip form process and the general constitution of a measuring system for carrying out the method of the present invention.

Referring to FIG. 1, a slide form assembly includes a plurality of panels 10, only two of which are shown in the drawing. The inner panels (for example the left-hand panels 10) and the outer panels (for example the right-hand panels 10) each are arranged side by side to define an enclosed space therebetween, a diameter of which space depends on the number, size and configuration of the panels 10. The inner and outer panels 10 are supported by respective yoke legs 12 of which upper ends are connected to each other by a beam 14. A portal column 16 is provided to support the beam 14 and a platform 18 which is fixed to the lower end of the column 16 and to which the yoke legs 12 are pivotably connected at substantially central portions thereof. Concrete is poured in the space defined within the panels 10 to construct a wall 20 having, for example, a cylindrical shape. Buried in the wall 20 is a rod 22 within which an end of a jack 24 extends. The jack 24 is mounted on the beam 14 and is adapted to elevate the whole assembly as the concrete pouring progresses. The above arrangement is substantially the same as the conventional slide form assembly.

A rod-shaped temperature sensor 28 is secured to the beam 14 substantially in the middle of the same.

Figure 2:
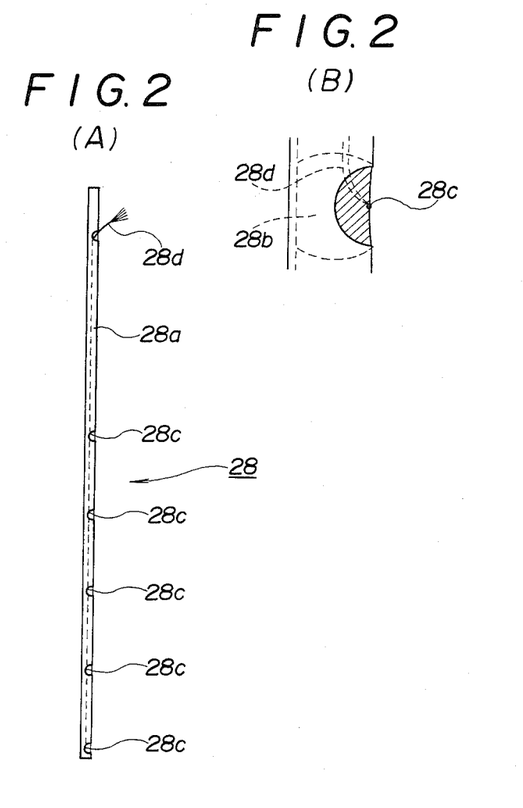
FIG. 2A and 2B are a perspective view and an enlarged fragmentary view, respectively, of an exemplary temperature sensor employed in the measuring system of FIG. 1.

As illustrated in detail in FIG. 2, the temperature sensor 28 comprises a tubular sheath 28a, a plurality of measuring elements 28c fixedly held with a caulking material 28b in through holes formed in the wall of the tubular sheath 28a, respectively, so as to be exposed to concrete, and lead wires 28d connected to the measuring elements 28c, respectively. In this temperature sensor, five measuring elements 28c, such as thermocouples, are arranged along the axial direction of the tubular sheath 28a at regular intervals, the lowermost element being positioned near the lower end of the tubular sheath 28a. The sheath 28a is attached to the beam 14 so that the lowermost measuring element and the uppermost measuring element are located at levels substantially corresponding to the lower end of the panel 10 and the upper surface of the concrete poured in the slide form, respectively.

An altimeter 30 is provided to measure the position of the slide form. The altimeter 30 comprises a rotary encoder 30a rotatably attached to the outer surface of one of the panels 10, and a wire 30c extended around the rotary encoder 30a, which wire 30c is anchored at one end to the ground and is wound at the other end around a wire reel 30b. The rotary encoder 30a is rotated by the wire 30c to provide pulses corresponding to the lift or height of the panel 10 as the same is moved upward. The lead wires 28d of the temperature sensor 28 are connected to a switching circuit 32 which selects the measured values given by the measuring elements 28c individually to give selected output signals to an arithmetic unit 34.

The arithmetic unit 34 is a so-called microcomputer comprising a CPU, RAMs, ROMs and interfaces. The output signal of the rotary encoder 30a also is given to the arithmetic unit 34. In FIG. 1, indicated at 36 is a display unit, on which the results of the operation are displayed.

A method of measuring the strength of the concrete poured in the space defined between the panels 10, by means of the thus constituted measuring system will be described hereinafter.

Figure 3:
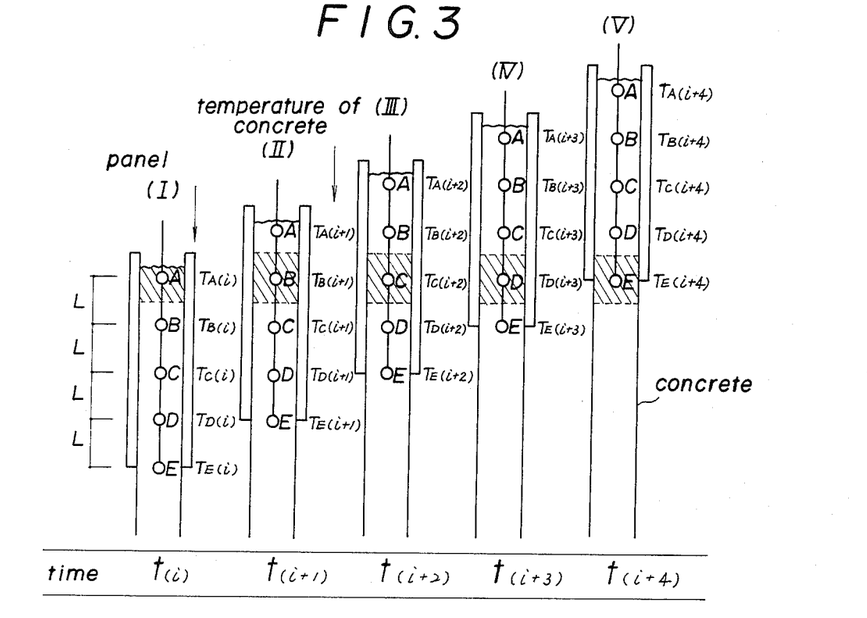
FIG. 3 is a diagrammatic illustration of assistance in explaining the measuring principle of the method of the present invention.

Referring to FIG. 3, letters A, B, C, D and E represent the first (top), second, third, fourth and fifth (bottom) measuring elements 28c, respectively. The spaced-apart measuring elements 28c are arranged at regular intervals L.

Suppose that at an optional time t(i) the bottom measuring element E is located substantially on the level of the lower end of the panels 10 and the top measuring element A is located just below the upper surface of the concrete which has been just poured in the slide form, as illustrated in FIG. 3-I. In this state, temperatures TA(i) to TE(i) measured by the elements A to E at a first plurality of points corresponding to the locations of the measuring elements when the slide form is at a lower position, respectively, are given in the form of signals through the switching circuit 32 to the arithmetic unit 34, where the temperature signals are stored in a memory. Since it is attached to the beam 14 joined to the panels 10, the temperature sensor 28 moves upward as the panels 10 are moved upward.

Next, suppose that the panels 10 have been moved upward a height L by a time t(i+1) as shown in FIG. 3-II, and hence the temperature sensor 28 has been lifted by the height L. The arithmetic unit 34 determines, on the basis of signals from the altimeter 30, whether the panels 10 have been moved the height L. At this time t(i+1), the measuring element B is located in a portion of the concrete corresponding to the shaded portion in FIG. 3-I. Temperatures TA(i+1) to TE(i+1) of the concrete are then measured by the respective elements A to E at a second plurality of points corresponding to the locations of the measuring elements when the slide form is at a higher position, and the information is transmitted through the switching circuit 32 to the arithmetic unit 34.

Figure 4:
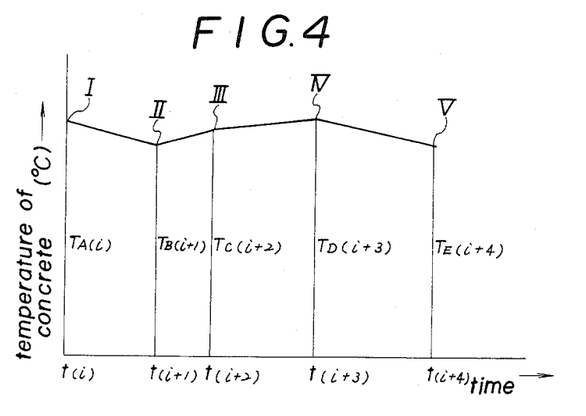
FIG. 4 is a graph showing a variation of temperature of concrete poured in a slide form with time.

Similarly, temperatures TA(i+2) to TE(i+2), TA(i+3) to TE(i+3) and TA(i+4) to TE(i+4) are measured by the elements A to E and recorded in the unit 34 at times t(i+2), t(i+3) and t(i+4), respectively, when the panels 10 are lifted by each height L. At the time t(i+4), i.e. at the time when the panels 10 were elevated by the height 4L, the shaded portion of the concrete which was placed in the slide form at the time t(i) is released from the panels 10, as illustrated in FIG. 3-V. The temperatures of this portion varying from TA(i)→TB(i+1)→TC(i+2)→TD(i+3)→TE(i+4) with the lapse of time from t(i)→t(i+1)→t(i+2)→t(i+3)→t(i+4), are measured sequentially by the elements 28c and signals corresponding to the measured temperatures are stored in the arithmetic unit 34 together with the record of times. Such variation of temperature of the shaded portion is illustrated in FIG. 4 which, however, should not be interpreted as showing test results but should be as used for explanation prupoges only. A temperature integral (Txt), that is, an integral of the measured temperatures and the period of time between t(i) and t(i+4), of the shaded portion is calculated by the following expression:

$$T \times t = [TA(i) + TB(i + 1)]/2 \times [t(i + 1) - t(i)] +$$
$$[TB(i + 1) + TC(i + 2)]/2 \times [t(i + 2) - t(i + 1)] +$$
$$[TC(i + 2) + TD(i + 3)]/2 \times [t(i + 3) - t(i + 2)] +$$
$$[TD(i + 3) + TE(i + 4)]/2 \times [t(i + 4) - t(i + 3)]$$

Similarly, the temperature integrals of portions corresponding to heights L, 2L and 3L from the lower end of the panel 10, respectively, are calculated.

Suppose that the panels 10 are raised by a height $\Delta L$ by an optional time $t(i+4+p)$ between the time $t(i+4)$ and a time $t(i+5)$ at which the panels 10 are moved upward by the height L, namely, $$t(i+4) \leq t(i+4+p) < t(i+5) \quad (1)$$

$$0 \leq \Delta L < L \quad (2)$$

Then, the temperature integral of a portion where the element E is located at the time $t(i+4+p)$ is calculated by an expression:

$$TE \times t(i+4+p) = \quad (3)$$

$$[\{TA(i) + TB(i+1)\}/2 \times (1 - \Delta L/L) + TA(i+1) \times$$

$$\Delta L/L] \times (1 - \Delta L/L) \times \{t(i+1) - t(i)\} +$$

$$[\{TB(i+1) + TC(i+2)\}/2 \times (1 - \Delta L/L + \{TA(i+1) +$$

$$TB(i+2)\}/2 \times \Delta L/L] \times \{t(i+2) - t(i+1)\} +$$

$$[\{TC(i+2) + TD(i+3)\}/2 \times (1 - \Delta L/L) + \{TB(i+2) +$$

$$TC(i+3)\}/2 \times \Delta L/L] \times \{t(i+3) - t(i+2)\} +$$

$$[\{TD(i+3) + TE(i+4)\}/2 \times (1 - \Delta L/L) + \{TC(i+3) +$$

$$TD(i+4)\}/2 \times \Delta L/L] \times \{t(i+4) - t(i+3)\} +$$

$$\{TE(i+4) \times (1 - \Delta L/L) + TD(i+4) \times \Delta L/L\} \times$$

$$\{t(i+4+p) - t(i+4)\}$$

Similarly, the temperature integral of a portion where the element D is located at the time $t(i+4+p)$ is calculated by an expression:

$$TD \times t(i+4+p) = \quad (4)$$

$$[\{TA(i+1) + TB(i+2)\}/2 \times (1 - \Delta L/L) + TA(i+2) \times$$

$$\Delta L/L] \times (1 - \Delta L/L) \times \{t(i+2) - t(i+1)\} +$$

$$[\{TB(i+2) + TC(i+3)\}/2 \times (1 - \Delta L/L) + \{TA(i+2) +$$

$$TB(i+3)\}/2 \times \Delta L/L] \times \{t(i+3) - t(i+2)\} +$$

$$[\{TC(i+3) + TD(i+4)\}/2 \times (1 - \Delta L/L) + \{TB(i+3) +$$

$$TC(i+4)\}/2 \times \Delta L/L] \times \{t(i+4) - t(i+3)\} +$$

$$\{TD(i+4) \times (1 - \Delta L/L) + TC(i+4) \times \Delta L/L\} \times$$

$$\{t(i+4+p) - t(i+4)\}$$

Figure 5:
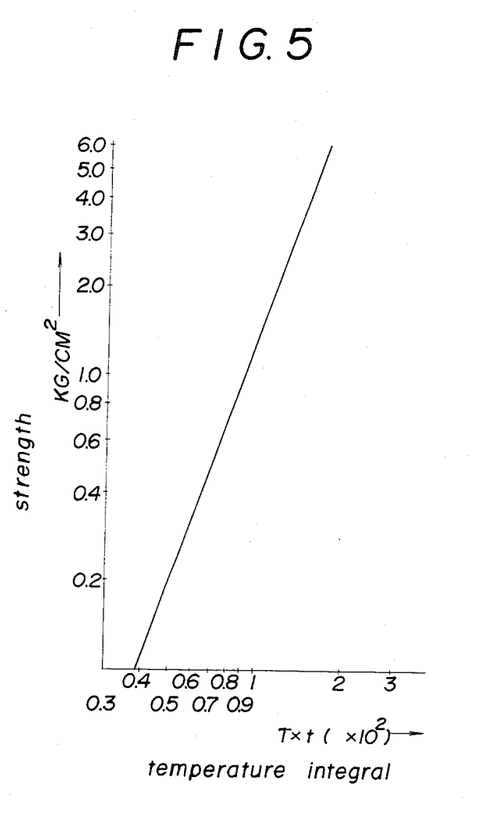
FIG. 5 is a graph showing the relation between the strength of concrete and the temperature integral.

Thus, the temperature integral $(T \times t)$ of the concrete poured in the slide form is obtained. Since the relation between the strength of concrete and the temperature integral is known accurately as shown in FIG. 5, by way of example, the strength of the concrete poured in the slide form can be determined on the basis of the temperature integral. FIG. 5 shows the relation between the temperature integral and the strength of a concrete of ordinary portland cement, having a water-to-cement ratio of 40%, which is published in "GUIDELINES ON THE PREPARATION, CONTROL AND QUALITY TEST OF CONCRETE", Nippon Kenchiku Gakkai.

Data representing the relation between the temperature integral and the strength of concrete for various classes of cement and water-to-cement ratios are written beforehand in the memory of the arithmetic unit 34. Accordingly, the strength of the concrete placed in the slide form is determined from the temperature integral $(T \times t)$ by the arithmetic unit 34, and the strength thus calculated is displayed on the display unit 36.

Figure 6:
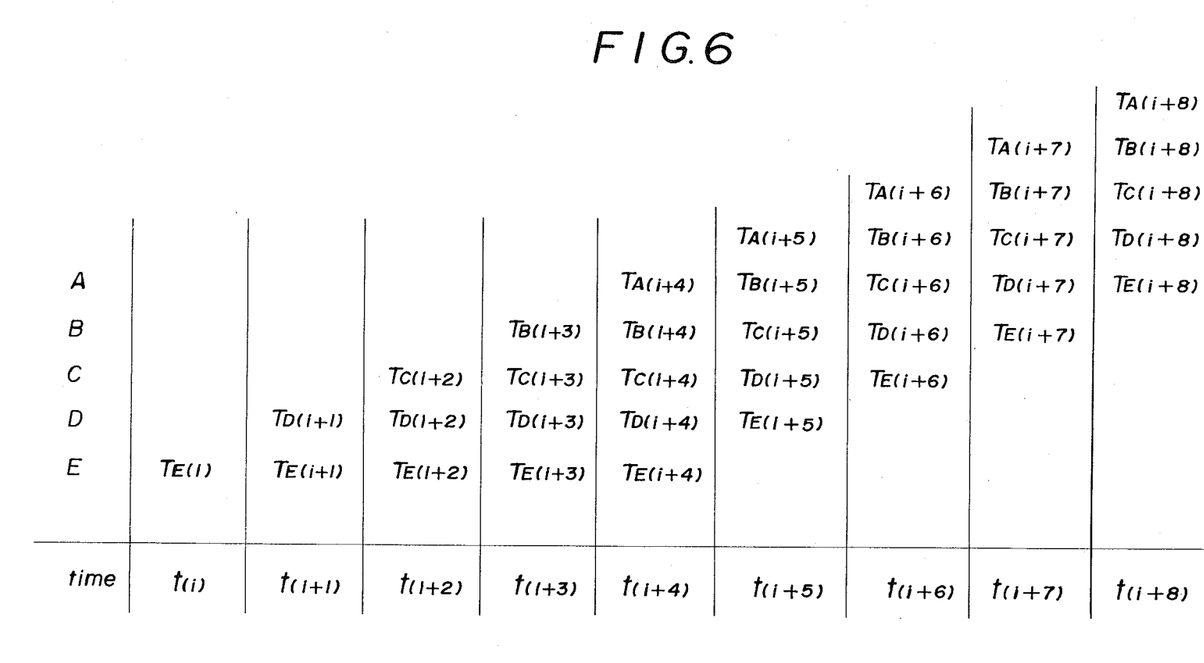
FIG. 6 is a diagram of assistance in explaining the measuring method of the invention when the slip form process is commenced.

The expressions mentioned above are used for calculating the temperature integral in a case in which the panels 10 are being moved upward. At the start of the slide form process, the panels 10, and hence the temperature sensor 28, are not moved upward until the concrete reaches the upper end of the panels 10. Accordingly, additional expressions are necessary. Referring to FIG. 6, concrete is poured to a level above the measuring element E at a time $t(i)$, and then to a level above the element D at a time $t(i+1)$. In this way, concrete is poured to a level above the element A by a time $t(i+4)$, namely to a level corresponding to the upper end of the panels 10. Since the panels 10 need not be raised until the concrete is poured up to the upper end of the panel 10, the measuring elements remain at their respective initial positions. After the time $t(i+4)$, concrete is poured in the slide form as the panels 10 are moved upward. At an optional time $t(i+4+p)$ before a time $t(i+5)$ by which the panels 10 are moved upward by a first height L, the temperature integral $TE \times t(i+4+p)$ of the bottom portion, namely, a portion in which the measuring element E is located, is calculated by an expression:

$$TE \times t(i+4+p) = \quad (5)$$

$$[\{TE(i) + TE(i+1)\}/2 \times (1 - \Delta L/L) + TD(i+1) \times$$

$$\Delta L/L] \times (1 - \Delta L/L) \times \{t(i+1) - t(i)\} +$$

$$[\{TE(i+1) + TE(i+2)\}/2 \times (1 - \Delta L/L) + \{TD(i+1) +$$

$$TD(i+2)\}/2 \times \Delta L/L] \times \{t(i+2) - t(i+1)\} +$$

$$[\{TE(i+2) + TE(i+3)\}/2 \times (1 - \Delta L/L) + \{TD(i+2) +$$

$$TD(i+3)\}/2 \times \Delta L/L] \times \{t(i+3) - t(i+2)\} +$$

$$[\{TE(i+3) + TE(i+4)\}/2 \times (1 - \Delta L/L) + \{TD(i+3) +$$

$$TD(i+4)\}/2 \times \Delta L/L] \times \{t(i+4) - t(i+3)\} +$$

$$\{TE(i+4) \times (1 - \Delta L/L) + TD(i+4) \times \Delta L/L\} \times$$

$$\{t(i+4+p) - t(i+4)\}$$

where $\Delta L$ is a height the panels 10 are raised from $t(i+4)$ to $t(i+4+p)$.

Similarly, the temperature integral of a portion above the lower end of the panels by the height L, where the measuring element D is located at the time $t(i+4+p)$, is expressed by:

$$TD \times t(i+4+p) = \quad (6)$$

$$[\{TD(i+1) + TD(i+2)\}/2 \times (1 - \Delta L/L) + TC(i+2) \times$$

$$\Delta L/L] \times (1 - \Delta L/L) \times \{t(i+2) - t(i+1)\} +$$

$$[\{TD(i+2) + TD(i+3)\}/2 \times (1 - \Delta L/L) + \{TC(i+2) +$$

$$TC(i+3)\}/2 \times \Delta L/L] \times \{t(i+3) - t(i+2)\} +$$

$$[\{TD(i+3) + TD(i+4)\}/2 \times (1 - \Delta L/L) + \{TC(i+3) +$$

$$TC(i+4)\}/2 \times \Delta L/L \times \{t(i+4) - t(i+3)\} +$$

$$\{TD(i+4) \times (1 - \Delta L/L) + TC(i+4) \times \Delta L/L\} \times$$

$$\{t(i + 4 + p) - t(i + 4)\}$$

The temperature integral TE×t(i+5+p) of a portion at the lower end of the panels, at an optional time t(i+5+p) between a time t(i+5) and a time t(i+6) by which the panels are lifted by another height L, is calculated by:

$$TE \times t(i + 5 + p) = \qquad (7)$$

$$[\{TD(i + 1) + TD(i + 2)\}/2 \times (1 - \Delta L/L) + TC(i + 2) \times$$

$$\Delta L/L] \times (1 - \Delta L/L) \times \{t(i + 2) - t(i + 1)\} +$$

$$[\{TD(i + 2) + TD(i + 3)\}/2 \times (1 - \Delta L/L) + \{TC(i + 2) +$$

$$TC(i + 3)\}/2 \times \Delta L/L] \times \{t(i + 3) - t(i + 2)\} +$$

$$[\{TD(i + 3) + TD(i + 4)\}/2 \times (1 - \Delta L/L) + \{TC(i + 3) +$$

$$TC(i + 4)\}/2 \times \Delta L/L] \times \{t(i + 4) - t(i + 3)\} +$$

$$[\{TD(i + 4) + TE(i + 5)\}/2 \times (1 - \Delta L/L) + \{TC(i + 4) +$$

$$TD(i + 5)\}/2 \times \Delta L/L] \times \{t(i + 5) - t(i + 4)\} +$$

$$\{TE(i + 5) \times (1 - \Delta L/L) + TD(i + 5) \times \Delta L/L\} \times$$

$$\{t(i + 5 + p) - t(i + 5)\}$$

Similarly, the temperature integral of a portion above the lower end of the panels by the height L, in which the measuring element D is located at the time t(i+5+p), is calculated by:

$$TD \times t(i + 5 + p) = \qquad (8)$$

$$[\{TC(i + 2) + TC(i + 3)\}/2 \times (1 - \Delta L/L) + TB(i + 3) \times$$

$$\Delta L/L] \times (1 - \Delta L/L) \times \{t(i + 3) - t(i + 2)\} +$$

$$[\{TC(i + 3) + TC(i + 4)\}/2 \times (1 - \Delta L/L) + \{TB(i + 3) +$$

$$TB(i + 4)\}/2 \times \Delta L/L] \times \{t(i + 4) - t(i + 3)\} +$$

$$[\{TC(i + 4) + TD(i + 5)\}/2 \times (1 - \Delta L/L) + \{TB(i + 4) +$$

$$TC(i + 5)\}/2 \times \Delta L/L] \times \{t(i + 5) - t(i + 4)\} +$$

$$\{TD(i + 5) \times (1 - \Delta L/L) + TC(i + 5) \times \Delta L/L\} \times$$

$$\{t(i + 5 + p) - t(i + 5)\}$$

The temperature integrals at times t(i+6+p) and t(i+7+p) can be calculated in a similar manner. At a time t(i+8), the measuring element E arrives at a position in the concrete poured at the time t(i+4). Therefore, Expressions (3) and (4) apply to the calculation of the temperature integral thereafter. The panels 10 remain stationary from the time t(i) to the time t(i+4) and the altimeter 30 does not provide any signal, while measured temperatures are stored in the memory through the manual operation of a keyboard.

Figure 7:
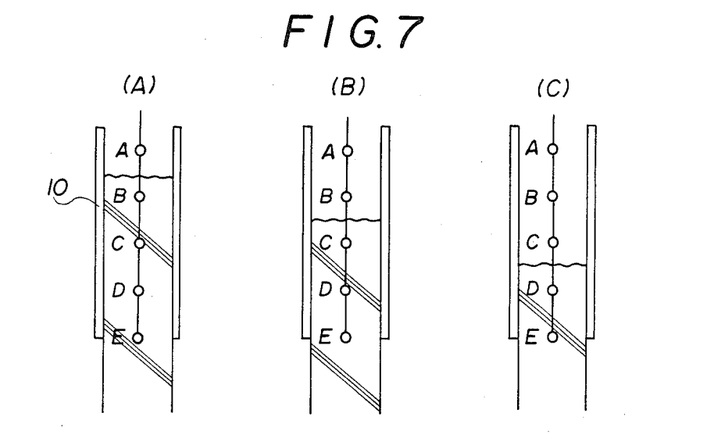
FIGS. 7A to 7C are illustrations showing the mode of restarting concrete pouring work.
Figure 8:
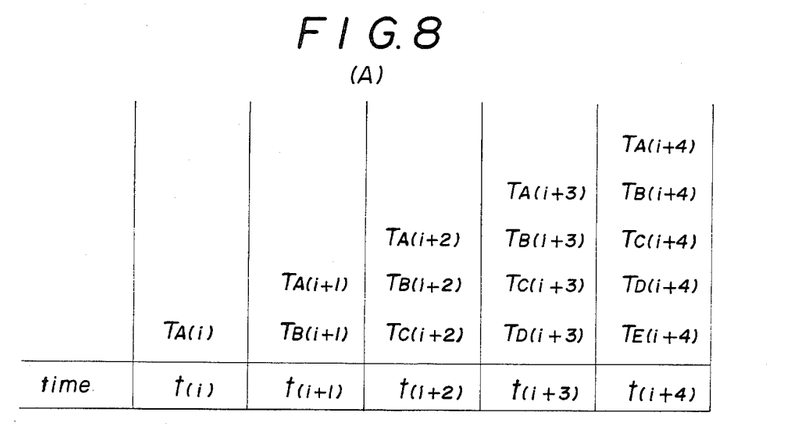
FIGS. 8A to 8C are diagrams of assistance in explaining the measuring method of the invention in case of restarting corresponding to FIGS. 7A to 7C, respectively.
Figure 8B:
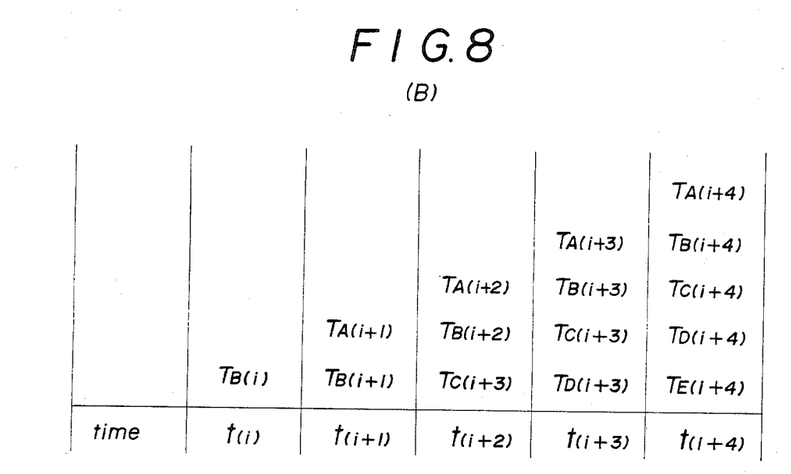
Figure 8C:
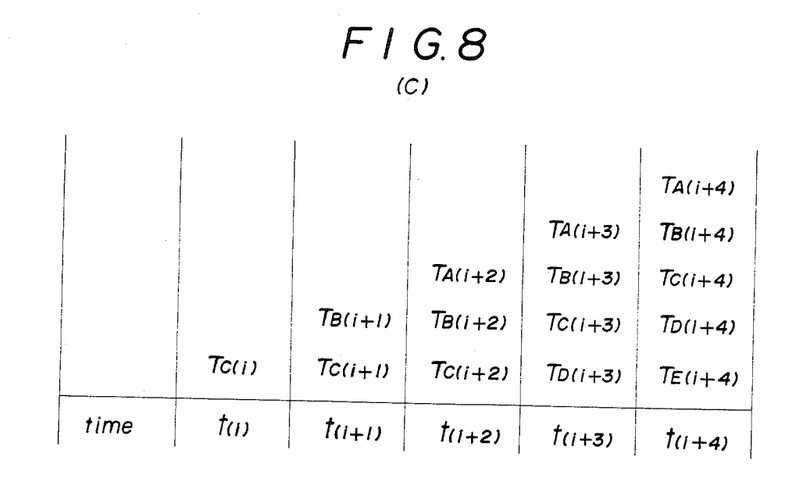

FIGS. 7 and 8 show a mode of temperature measurement in restarting concrete pouring after the concrete poured previously halfway up the panels has set completely, for example, in restarting concrete pouring after the interruption of concrete pouring on the preceding day. In the case of FIG. 7A, concrete is poured to a level above the measuring element A at a time t(i) and a temperature TA(i) of the concrete at the time t(i) is stored in the memory through the manual operation of the keyboard. In the case of FIG. 7B, concrete is poured to a level above the measuring element B and a level above the element A at a time t(i) and at a time t(i+1), respectively. In the case of FIG. 7C, concrete is poured to levels above the elements C, B and A at times t(i), t(i+1) and t(i +2), respectively, and the temperatures of the portions corresponding to the elements C, B and A are stored in the memory through the manual operation of the keyboard. Thereafter, the altimeter 30 provides signals as panels are moved upward, and thereby the temperature is measured and stored in the memory automatically. In the case of FIG. 7A, the temperature integral is calculated by:

$$TA \times t(i + p) = TA(i) \times \{t(i + p) - t(i)\} \qquad (9)$$

$$TB \times t(i + 1 + p) = \{TA(i) + TB(i + 1)\}/2 \times \{t(i + 1) - \qquad (10)$$

$$t(i)\} + TB(i + 1) \times \{t(i + 1 + p) - t(i + 1)\}$$

$$TC \times t(i + 2 + p) = \{TA(i) + TB(i + 1)\}/2 \times \{t(i + 1) - \qquad (11)$$

$$t(i)\} + \{TB(i + 1) + TC(i + 2)\}/2 \times$$

$$\{t(i + 2) - t(i + 1)\} + TC(i + 2) \times \{t(i + 2 + p) - t(i + 2)\}$$

$$TD \times t(i + 3 + p) = \{TA(i) + TB(i + 1 + \}/2 \times \{t(i + \qquad (12)$$

$$1) - t(i)\} + \{TB(i + 1) + TC(i + 2)\}/2 \times$$

$$\{t(i + 2) - t(i + 1)\} + \{TC(i + 2) +$$

$$TD(i + 3)\}/2 \times \{t(i + 3) - t(i + 2)\} +$$

$$TD(i + 3) \times \{t(i + 3 + p) - t(i + 3)\}$$

Expressions for the cases of FIGS. 7B and 7C will be omitted, since the manner of calculation for those cases may be inferred from the expression for the case of FIG. 7A.

The temperature integral after the time t(i+4), (t(i+5) for the case of FIG. 7B and t(i+6) for the case of FIG. 7C), can be calculated by Expressions (3) and (4).

Although the temperature sensor 28 employed in the above embodiment is provided with five measuring elements 28c, naturally, the number of the elements 28c is not limited thereto, but the temperature sensor 28 may be provided with any optional number of the elements.

Figure 9:
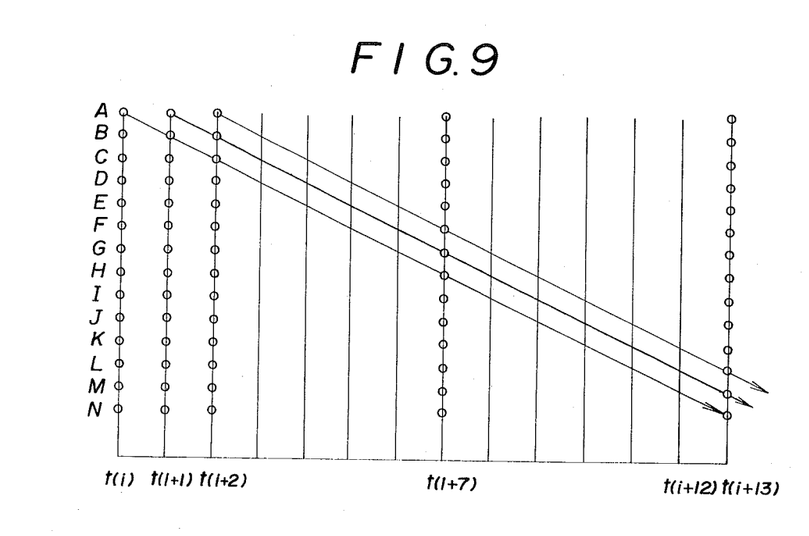
FIGS. 9 to 11 are diagrams of assistance in explaining the principle of measurement in another embodiment according to the present invention.
Figure 10:
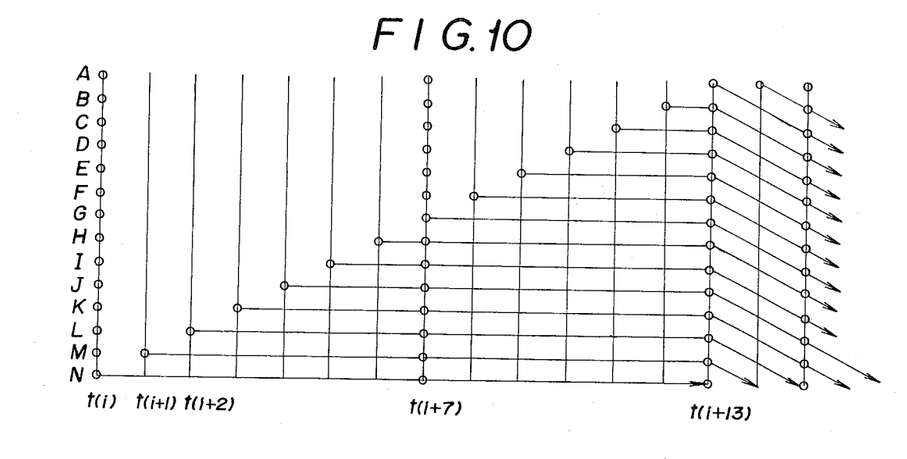
Figure 11:
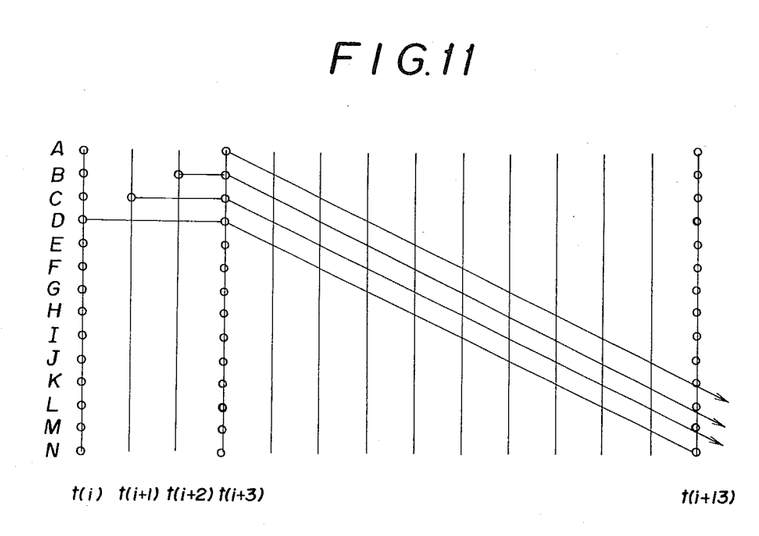

FIGS. 9 to 11 show a mode of temperature measurement by means of a temperature sensor having fourteen measuring elements 28c. FIGS. 9, 10 and 11 show modes of temperature measurement during the upward movement of the panels 10, at the start of concrete pouring, and at the restart of concrete pouring after interruption, respectively. Referring to FIG. 9, the temperature of the concrete poured at a time t(i) is measured first with the element A, and then the temperature is measured sequentially with the elements B, C, . . . until finally the temperature is measured with the element N at a time t(i+13). Accordingly, the temperature integral of the concrete can be calculated by expressions produced on the same basis as the above-mentioned Expressions (3) and (4). In the case of FIG. 10, the panels 10 remain stationary between the time t(i) and the time t(i+13) and the upward movement of the panels is started after the time t(i+13). Accordingly, the temperature integrals of the concrete at times t(i+13+p), t(i+14+p), . . . can be calculated by expressions produced on the same basis as Expressions (5) to (8).

FIG. 11 shows a mode of temperature measurement when concrete pouring is restarted after the concrete which was previously poured up to a level about the element E has set completely. In this case, the upward movement of the panels is started at a time t(i+3). Accordingly, the conception for the calculation of temperature integral in the above restarting occasion applies also to this case.

It is also possible to make the length of the temperature sensor 28 and the number of the measuring elements 28c variable thereby to vary the number of measuring points according to the condition of the slip form process.

As is apparent from the foregoing description of the exemplary application of the method of the present invention, according to the present invention the strength of concrete placed in the slide form is measured on the basis of the temperature integral of the concrete of time from the pouring to the release from the slide form, and hence the strength of the concrete can be accurately determined.

Furthermore, since the temperature sensor which provides temperature data for the calculation of the temperature integral moves upward together with the slide form, continuous temperature measurement is possible without interrupting the upward movement of the slide form, which improves the efficiency of concrete pouring work remarkably.

Although the present invention has been described with reference to the preferred embodiments thereof, many modifications and alterations may be made within the spirit of the invention.

What is claimed is:

1. In a slip form process in which a slide form is moved upward after concrete poured therein has set to a degree to provide a sufficient strength, a method of measuring the strength of said concrete comprising the steps of:
   measuring a position of said slide form by an altimeter
   measuring a temperature of said concrete by a temperature sensor movable with said slide form and inserted into said concrete, said temperature sensor having arranged in an axial direction thereof a plurality of spaced-apart measuring elements separated from each other by a predetermined distance and adapted to operate when said slide form is moved upward by said predetermined distance, whereby the temperature of a particular point of said concrete is measured in sequence by said plurality of measuring elements;
   calculating an integral of the temperature over time of said concrete within said slide form, by an arithmetic unit on the basis of data given by said temperature sensor and said altimeter; and
   determining strength of said concrete based on said integral.

2. A method as claimed in claim 1, wherein said arithmetic unit includes a memory in which data representing the relation between said integral and the strength of the concrete is stored, and the strength is determined by said arithmetic unit.

3. A method as claimed in claim 1, wherein signals from said measuring elements of said temperature sensor are selectively sent to said arithmetic unit through a switching circuit.

4. A method as claimed in claim 1, wherein said altimeter comprises a rotary encoder attached to said slide form for movement therewith, and a wire extending around said rotary encoder and anchored at one end to the ground and at the other end to a wire reel, and the position of said slide form is measured by the rotation of said rotary encoder.

5. A method of determining the strength of concrete cast by a slip form process in which a slide form is periodically moved from a lower position to a higher position after concrete poured into the slide form at each lower position attains a strength sufficient to support itself and the slide form, comprising:
   measuring the temperature of the concrete at at least one particular point of the concrete with a temperature sensor fixed to said slide form for movement therewith, said temperature sensor including a plurality of spaced-apart measuring elements separated from each other by a predetermined distance, a different one of said plurality of spaced-apart measuring elements successively measuring the temperature of the concrete at said one particular point each time said slide form is moved from a lower position to a higher position by an amount equal to said predetermined distance;
   calculating an integral of the temperature over time for said one particular point of the concrete; and
   determining the strength of the concrete at least at said one particular point on the basis of the integral for said one particular point.

6. The method of claim 1, wherein the temperature of the concrete is measured at a first plurality of points corresponding to the locations of said measuring elements when said slide form is at said lower position and the temperature of the concrete is measured at a second plurality of points corresponding to the locations of said measuring elements when said slide form is moved said predetermined distance to said higher position, said one particular point being one of said first plurality of points and one of said second plurality of points.

7. The method of claim 6, wherein said integral is calculated for each of said second plurality of points and is converted to a temperature integral by an arithmetic unit and said temperature integral is compared to a known temperature integral versus known strength for the type of concrete being cast by said slip form process.

8. The method of claim 5, wherein the integral of the temperature over time is calculated for a plurality of points corresponding to the locations of said measuring elements by measuring the temperature of each of said measuring elements when said temperature sensor is at said lower position and when said temperature sensor is at said higher position, signals corresponding to said temperatures being sent to an arithmetic unit by means of switching circuit which sequentially sends a signal corresponding to the measured temperature at each of said measuring elements to said arithmetic unit, said arithmetic unit calculating measured temperature versus time data for said plurality of points, converting the temperature versus time data to the integral of temperature over time and determining the strength of the concrete by comparing the integral to a known temperature integral versus known strength for the type of concrete being cast by said slip form process.

9. The method of claim 5, wherein the height of said slide form is measured by an altimeter, whereby said slide form can be moved said predetermined distance from said lower position to said higher position.

10. The method of claim 9, wherein said altimeter comprises a rotary encoder attached to said slide form for movement therewith and a wire anchored at one end thereof to a fixed support surface and at the other end thereof to a rotatable wire reel with an intermediate portion of said wire rotatably connected to said encoder for rotating said encoder when said slide form is periodically moved from each lower position to each higher position.

11. An apparatus for determining the strength of concrete cast by a slip form process in which a slide form is periodically moved from a lower position to a higher position after concrete poured into the slide form at each lower position attains a strength sufficient to support itself and the slide form, comprising:

a temperature sensor adapted to be fixed to the slide form for movement therewith, said temperature sensor including a plurality of spaced-apart measuring elements separated from each other by a predetermined distance in an axial direction;

an altimeter adapted to be fixed to the slide form for movement therewith;

an arithmetic unit means electrically connected to said altimeter and said temperature sensor for determining the strength of the concrete on the basis of data supplied to said arithmetic unit means from said altimeter and said temperature sensor; and a switching circuit means electrically connecting said temperature sensor to said arithmetic unit means for sequentially sending signals from each of said measuring elements to said arithmetic unit means, whereby an integral of the temperature over time of the concrete within the slide form for at least one particular point of the concrete can be calculated and compared to predetermined values for determining the strength of the concrete.

* * * * *